(12) United States Patent
Pratt

(10) Patent No.: US 7,563,808 B2
(45) Date of Patent: *Jul. 21, 2009

(54) METHODS FOR TREATING COGNITIVE IMPAIRMENTS OR DEMENTIA

(75) Inventor: Raymond Pratt, Leonia, NJ (US)

(73) Assignee: Eisai Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/732,349

(22) Filed: Dec. 11, 2003

(65) Prior Publication Data

US 2004/0122051 A1 Jun. 24, 2004

Related U.S. Application Data

(63) Continuation of application No. 10/232,406, filed on Sep. 3, 2002, now Pat. No. 6,689,795, which is a continuation of application No. 09/947,086, filed on Sep. 4, 2001, now Pat. No. 6,458,807, which is a continuation of application No. PCT/US01/07027, filed on Mar. 5, 2001.

(60) Provisional application No. 60/259,226, filed on Jan. 3, 2001, provisional application No. 60/220,783, filed on Jul. 25, 2000, provisional application No. 60/197,610, filed on Apr. 18, 2000, provisional application No. 60/186,744, filed on Mar. 3, 2000.

(51) Int. Cl.
*A61K 31/445* (2006.01)

(52) U.S. Cl. ...................................... 514/319

(58) Field of Classification Search .................. 514/319
See application file for complete search history.

(56) References Cited

U.S. PATENT DOCUMENTS

| | | | |
|---|---|---|---|
| 4,826,843 A * | 5/1989 | Mattson et al. | 514/252.03 |
| 4,895,841 A | 1/1990 | Sugimoto et al. | |
| 5,486,512 A * | 1/1996 | Gregor | 514/214.02 |
| 5,985,864 A | 11/1999 | Imai et al. | |
| 6,140,321 A | 10/2000 | Imai et al. | |
| 6,193,993 B1 | 2/2001 | Murahashi et al. | |
| 6,245,911 B1 | 6/2001 | Imai et al. | |
| 6,252,081 B1 | 6/2001 | Iimura | |
| 6,372,760 B1 | 4/2002 | Kato et al. | |
| 6,455,544 B1 | 9/2002 | Friedhoff et al. | |
| 6,458,807 B1 | 10/2002 | Pratt | |
| 6,482,838 B2 | 11/2002 | Pratt | |
| 6,521,639 B1 | 2/2003 | Murahashi et al. | |
| 6,576,646 B1 * | 6/2003 | Pratt | 514/319 |
| 6,576,677 B1 | 6/2003 | Ukai et al. | |
| 6,608,088 B1 | 8/2003 | Nicolodi et al. | |
| 6,689,795 B2 * | 2/2004 | Pratt | 514/319 |
| 2001/0036949 A1 | 11/2001 | Coe et al. | |
| 2003/0027841 A1 | 2/2003 | Murahashi et al. | |

FOREIGN PATENT DOCUMENTS

| | | |
|---|---|---|
| JP | 4-21670 | 1/1992 |
| JP | 4-187674 | 7/1992 |
| WO | WO 97/46527 | 6/1997 |
| WO | WO 97/46526 | 12/1997 |
| WO | WO 98/39000 | 9/1998 |
| WO | WO 99/36405 | 7/1999 |
| WO | WO 01/66096 A2 | 9/2001 |
| WO | WO 03/024450 | 3/2003 |
| WO | WO 03/024456 | 3/2003 |
| WO | WO 03/032914 | 4/2003 |
| WO | WO 03/092606 | 11/2003 |
| WO | WO 2004/034963 | 4/2004 |

OTHER PUBLICATIONS

Medline Abstract of McGeer et al., J. of Neural Transmission, Suppl. (1998), 54 159-66.*
Harrison's Principles of Internal Medicine, 13th edition, vol. 1, published 1994 by McGraw-Hill, Inc. (NY), pp. 137-146.*

(Continued)

*Primary Examiner*—Raymond J Henley, III
(74) *Attorney, Agent, or Firm*—Clark & Elbing LLP

(57) ABSTRACT

The invention describes novel methods for treating and preventing dementia caused by vascular diseases; dementia associated with Parkinson's disease; Lewy Body dementia; AIDS dementia; mild cognitive impairments; age-associated memory impairments; cognitive impairments and/or dementia associated with neurologic and/or psychiatric conditions, including epilepsy, brain tumors, brain lesions, multiple sclerosis, Down's syndrome, Rett's syndrome, progressive supranuclear palsy, frontal lobe syndrome, and schizophrenia and related psychiatric disorders; cognitive impairments caused by traumatic brain injury, post coronary artery by-pass graft surgery, electroconvulsive shock therapy, and chemotherapy, administering a therapeutically effective amount of at least one of the cholinesterase inhibitor compounds described herein. The invention also describes novel methods for treating and preventing delirium, Tourette's syndrome, myasthenia gravis, attention deficit hyperactivity disorder, autism, dyslexia, mania, depression, apathy, and myopathy associated with diabetes by administering a therapeutically effective amount of at least one of the cholinesterase inhibitor compounds described herein. The invention also describes novel methods for delaying the onset of Alzheimer's disease, for enhancing cognitive functions, for treating and preventing sleep apnea, for alleviating tobacco withdrawal syndrome, and for treating the dysfunctions of Huntington's Disease by administering a therapeutically effective amount of at least one of the cholinesterase inhibitor compounds described herein. A preferred cholinesterase inhibitor for use in the methods of the invention is donepezil hydrochloride or ARICEPT®.

14 Claims, No Drawings

OTHER PUBLICATIONS

Berger-Sweeney, "The Effects of Neonatal Basal Forebrain Lesions on Cognition: Towards Understanding the Developmental Role of the Cholinergic Basal Forebrain", Int. J. Devl. Neuroscience, vol. 16, Nos. 7/8, pp. 603-612, 1998.*

McGeer et al., "Mechanisms of cell death in Alzheimer's disease—immunopathology", J. Neural Trasm. (1998) [Suppl] 54: 159-166.*

Mendez et al, Journal of Neuropsychiatry and Clinical Neuroscience, 11(2):268-270 (1999).

Hasegawa et al, Folia Pharmacologica Japonica, 114(6):327-336 (Dec. 1999).

PCT International Search Report for PCT/US01/07027 (Aug. 14, 2001).

Diagnostic and Statistical Manual of Mental Disorders, 4th Ed., American Psychiatric Association, pp. 163-164 (2000).

Priya S. Kishnani et al; Cholinergic Therapy for Down's Syndrome, The Lancet, vol. 353, Mar. 27, 1999, pp. 1064-1065.

* cited by examiner

METHODS FOR TREATING COGNITIVE IMPAIRMENTS OR DEMENTIA

RELATED APPLICATIONS

This application is a continuation of U.S. application Ser. No. 10/232,406 filed Sep 3, 2002, issued as U.S. Pat No. 6,689,795, which is a continuation of U.S. application Ser. No. 09/947,086 filed Sep 4, 2001, issued as U.S. Pat No. 6,458,807, which is a continuation of PCT Application No. PCT/US01/07027 filed Mar 5, 2001, which claims priority to U.S. Provisional Application No. 60/259,226 filed Jan 3, 2001, U.S. Provisional Application No. 60/220,783 filed Jul 25, 2000, U.S. Provisional Application No. 60/197,610 filed Apr 18, 2000, and U.S. Provisional Application No. 60/186,744 filed Mar 3, 2000. This application is also related, but does not claim priority, to U.S. Pat. No. 6,482,838 and U.S. Pat. No. 6,576,646.

FIELD OF THE INVENTION

The invention describes novel methods for treating and preventing dementia caused by vascular diseases; dementia associated with Parkinson's disease; Lewy Body dementia; AIDS dementia; mild cognitive impairments; age-associated memory impairments; cognitive impairments and/or dementia associated with neurologic and/or psychiatric conditions, including epilepsy, brain tumors, brain lesions, multiple sclerosis, Down's syndrome, Rett's syndrome, progressive supranuclear palsy, frontal lobe syndrome, and schizophrenia and related psychiatric disorders; cognitive impairments caused by traumatic brain injury, post coronary artery by-pass graft surgery, electroconvulsive shock therapy, and chemotherapy, by administering a therapeutically effective amount of at least one of the cholinesterase inhibitor compounds described herein. The invention also describes novel methods for treating and preventing delirium, Tourette's syndrome, myasthenia gravis, attention deficit hyperactivity disorder, autism, dyslexia, mania, depression, apathy, and myopathy associated with or caused by diabetes by administering a therapeutically effective amount of at least one of the cholinesterase inhibitor compounds described herein. The invention also describes novel methods for delaying the onset of Alzheimer's disease, for enhancing cognitive functions, for treating and preventing sleep apnea, for alleviating tobacco withdrawal syndrome, and for treating the dysfunctions of Huntington's Disease by administering a therapeutically effective amount of at least one of the cholinesterase inhibitor compounds described herein. A preferred cholinesterase inhibitor for use in the methods of the invention is donepezil hydrochloride or ARICEPT®.

BACKGROUND OF THE INVENTION

Novel cholinesterase inhibitors are described in U.S. Pat. No. 4,895,841 and WO 98/39000, the disclosures of which are incorporated by reference herein in their entirety. The cholinesterase inhibitors described in U.S. Pat. No. 4,895,841 include donepezil hydrochloride or ARICEPT®, which has proven to be a highly successful drug for the treatment of Alzheimer's disease.

There is a need in the art for new and improved treatments for other diseases, disorders, and syndromes that are characterized by symptoms of dementia and/or cognitive impairments. The invention is directed to these, as well as other, important ends.

SUMMARY OF THE INVENTION

The invention describes novel methods for treating and preventing dementia associated with or caused by vascular diseases by administering to a patient a therapeutically effective amount of at least one of the cholinesterase inhibitor compounds described herein.

The invention describes novel methods for treating and preventing dementia associated with or caused by Parkinson's disease by administering to a patient a therapeutically effective amount of at least one of the cholinesterase inhibitor compounds described herein.

The invention describes novel methods for treating and preventing the dementia associated with or caused by Lewy Body dementia by administering to a patient a therapeutically effective amount of at least one of the cholinesterase inhibitor compounds described herein.

The invention describes novel methods for treating and preventing AIDS dementia by administering to a patient a therapeutically effective amount of at least one of the cholinesterase inhibitor compounds described herein.

The invention describes novel methods for treating and preventing mild (minor) cognitive impairments, age-associated memory impairments, and/or for delaying the onset of Alzheimer's disease by administering to a patient a therapeutically effective amount of at least one of the cholinesterase inhibitor compounds described herein.

The invention describes novel methods for treating and preventing cognitive impairments and/or dementia associated with neurologic and/or psychiatric conditions by administering to a patient a therapeutically effective amount of at least one of the cholinesterase inhibitor compounds described herein.

The invention describes novel methods for treating and preventing cognitive impairments and/or dementia associated with epilepsy (including cognitive impairments and/or dementia caused by or associated with the treatments for epilepsy) by administering to a patient a therapeutically effective amount of at least one of the cholinesterase inhibitor compounds described herein.

The invention describes novel methods for treating and preventing cognitive impairments and/or dementia associated with or caused by brain tumors by administering to a patient a therapeutically effective amount of at least one of the cholinesterase inhibitor compounds described herein.

The invention describes novel methods for treating and preventing cognitive impairments and/or dementia associated with or caused by brain lesions or other inflammatory brain diseases by administering to a patient a therapeutically effective amount of at least one of the cholinesterase inhibitor compounds described herein.

The invention describes novel methods for treating and preventing cognitive impairments and/or dementia associated with or caused by multiple sclerosis by administering to a patient a therapeutically effective amount of at least one of the cholinesterase inhibitor compounds described herein.

The invention describes novel methods for treating and preventing cognitive impairments and/or dementia associated with or caused by Down's syndrome by administering to a patient a therapeutically effective amount of at least one of the cholinesterase inhibitor compounds described herein.

The invention describes novel methods for treating and preventing cognitive impairments and/or dementia associated with or caused by Rett's syndrome by administering to a patient a therapeutically effective amount of at least one of the cholinesterase inhibitor compounds described herein.

The invention describes novel methods for treating and preventing cognitive impairments and/or dementia associated with or caused by progressive supranuclear palsy by administering to a patient a therapeutically effective amount of at least one of the cholinesterase inhibitor compounds described herein.

The invention describes novel methods for treating and preventing cognitive impairments and/or dementia associated with or caused by frontal lobe syndrome by administering to a patient a therapeutically effective amount of at least one of the cholinesterase inhibitor compounds described herein.

The invention describes novel methods for treating and preventing cognitive impairments and/or dementia associated with or caused by schizophrenia and related psychiatric disorders by administering to a patient a therapeutically effective amount of at least one of the cholinesterase inhibitor compounds described herein.

The invention describes novel methods for treating and preventing cognitive impairments and/or dementia caused by antipsychotic medications by administering to a patient a therapeutically effective amount of at least one of the cholinesterase inhibitor compounds described herein.

The invention describes novel methods for treating and preventing cognitive impairments caused by traumatic brain injury (e.g., post head trauma) by administering to a patient a therapeutically effective amount of at least one of the cholinesterase inhibitor compounds described herein.

The invention describes novel methods for treating and preventing cognitive impairments caused by post coronary artery by-pass graft surgery or by ischemic vascular disease by administering to a patient a therapeutically effective amount of at least one of the cholinesterase inhibitor compounds described herein.

The invention describes novel methods for treating and preventing cognitive impairments associated with or caused by electroconvulsive shock therapy (including cognitive impairments caused by the seizures which can be a side-effect of electroconvulsive shock therapy) by administering to a patient a therapeutically effective amount of at least one of the cholinesterase inhibitor compounds described herein.

The invention describes novel methods for treating and preventing cognitive impairments associated with or caused by chemotherapy by administering to a patient a therapeutically effective amount of at least one of the cholinesterase inhibitor compounds described herein.

The invention describes novel methods for treating and preventing delirium by administering to a patient a therapeutically effective amount of at least one of the cholinesterase inhibitor compounds described herein.

The invention describes novel methods for treating and preventing Tourette's syndrome by administering to a patient a therapeutically effective amount of at least one of the cholinesterase inhibitor compounds described herein.

The invention describes novel methods for treating and preventing myasthenia gravis (including Lambert-Eaton syndrome) by administering to a patient a therapeutically effective amount of at least one of the cholinesterase inhibitor compounds described herein.

The invention describes novel methods for treating and preventing the cognitive impairments and/or attentional symptoms associated with or caused by attention deficit hyperactivity disorder (ADHD) by administering to a patient a therapeutically effective amount of at least one of the cholinesterase inhibitor compounds described herein.

The invention describes novel methods for treating and preventing autism by administering to a patient a therapeutically effective amount of at least one of the cholinesterase inhibitor compounds described herein.

The invention describes novel methods for treating and preventing dyslexia by administering to a patient a therapeutically effective amount of at least one of the cholinesterase inhibitor compounds described herein.

The invention describes novel methods for treating and preventing mania and/or depression in patients by administering to a patient a therapeutically effective amount of at least one of the cholinesterase inhibitor compounds described herein.

The invention describes novel methods for treating and preventing apathy by administering to a patient a therapeutically effective amount of at least one of the cholinesterase inhibitor compounds described herein.

The invention describes novel methods for treating and preventing myopathy associated with or caused by diabetes by administering to a patient a therapeutically effective amount of at least one of the cholinesterase inhibitor compounds described herein.

The invention also describes novel methods for enhancing cognitive functions by administering to a patient a therapeutically effective amount of at least one of the cholinesterase inhibitor compounds described herein.

The invention also describes novel methods of treating and preventing sleep apnea by administering to a patient a therapeutically effective amount of at least one of the cholinesterase inhibitor compounds described herein.

The invention also describes novel methods for alleviating tobacco withdrawal syndrome by administering to a patient a therapeutically effective amount of at least one of the cholinesterase inhibitor compounds described herein.

The invention also provides novel methods for treating the cognitive and/or behavioral dysfunctions in Huntington's disease by administering to a patient a therapeutically effective amount of at least one of the cholinesterase inhibitor compounds described herein.

The invention is described in more detail below.

DETAILED DESCRIPTION OF THE INVENTION

"Patient" refers to animals, preferably mammals, more preferably humans. The term "patient" includes adults and children, and includes men and women. Children includes neonates, infants, and adolescents.

"Cognitive impairment" refers to an acquired deficit in one or more of memory function, problem solving, orientation and/or abstraction that impinges on an individual's ability to function independently.

"Dementia" refers to a global deterioration of intellectual functioning in clear consciousness, and is characterized by one or more symptoms of disorientation, impaired memory, impaired judgment, and/or impaired intellect. The symptoms of "dementia" are generally worse than, and can encompass, the symptoms of "cognitive impairment."

"Dementia associated with or caused by vascular diseases," also referred to as vascular dementia, generally refers to cerebrovascular diseases (e.g., infarctions of the cerebral hemispheres), which generally have a fluctuating course with periods of improvement and stepwise deterioration. "Vascular dementia" can include one or more symptoms of disorientation, impaired memory and/or impaired judgment. Early markers of vascular dementia can include urinary dysfunction and/or gait disturbances. Vascular dementia can be caused by discrete multiple infarctions, or other vascular causes including, for example, autoimmune vasculitis, such as that found in systemic lupus erythematosus; infectious vasculitis, such as Lyme's disease; recurrent intracerebral hemorrhages; and/or strokes. "Vascular dementia" can also be referred to as cerebrovascular dementia.

"Parkinson's disease" is a neurological syndrome usually resulting from deficiency of the neurotransmitter dopamine as the consequence of degenerative, vascular or inflammatory changes in the basal ganglia, and is characterized by rhythmical muscular tremors, rigidity of movement, fesination, droopy posture and/or masklike facies. In preferred embodiments, the invention is directed to methods of treating and preventing dementia, as defined herein, that is caused by or associated with Parkinson's disease.

"Lewy body dementia" is characterized by one or more symptoms of the development of dementia with features overlapping those of Alzheimer's disease; development of features of Parkinson's disease; and/or early development of hallucinations. Lewy body dementia is generally characterized by day-to-day fluctuations in the severity of the symptoms. The name for the disease comes from the presence of abnormal lumps which develop inside nerve cells called Lewy bodies.

"AIDS dementia" is caused by the complications associated with HIV disease or AIDS. Symptoms associated with AIDS dementia can include one or more of the following: headaches, retro-orbital pain, photophobia, depression, mania, irritability, psychosis, mental slowing, inattention, apathy, reduced concentration, forgetfulness, motor abnormalities, gait abnormalities (ataxia), altered personality, disorientation, impaired memory, impaired judgment, and/or impaired intellect.

"Mild cognitive impairments" refer to one or more minor symptoms of disorientation, impaired memory, impaired judgment, and/or impaired intellect. The elderly often suffer from mild cognitive impairments, usually memory impairments, that do not rise to the level of an Alzheimer's disease diagnosis. The invention also describes methods of delaying the onset of Alzheimer's disease (including preventing the onset of Alzheimer's disease) by administering to a patient the cholinesterase inhibitor compounds described herein, preferably by administering the cholinesterase inhibitor compounds to a patient suffering from age-associated memory impairments.

"Cognitive impairments and/or dementia associated with epilepsy" refers to cognitive impairments, as defined herein, and/or dementia, as defined herein, that are associated with or caused by epilepsy. The cholinesterase inhibitors described herein are also useful in methods for treating the side-effects (e.g., cognitive impairments and/or dementia) that are caused by the drugs that are used to treat epilepsy.

"Cognitive impairments associated with brain tumors" refers to cognitive impairments, as defined herein, that are caused by or associated with brain tumors.

"Cognitive impairments associated with brain lesions" refers to cognitive impairments, as defined herein, that are caused by or associated with brain lesions or inflammatory diseases of the brain.

"Multiple sclerosis" is a disease caused by the occurrence of patches of sclerosis (e.g., plaques) in the brain and spinal cord, and is characterized by some degree of paralysis, tremor, nystagmus and/or disturbances of speech. The symptoms of multiple sclerosis are dependent upon the location of the lesions on the brain. The invention is preferably directed to methods of treating and preventing cognitive impairments, as defined herein, and/or dementia, as defined herein, that are associated with or caused by multiple sclerosis.

"Down's syndrome" is a syndrome of mental retardation associated with a plethora of abnormalities caused by representation of chromosome 21 (or a critical portion thereof) three times instead of twice in some or all cells. In preferred embodiments, the invention is directed to methods of treating and preventing cognitive impairments, as defined herein, and/or dementia, as defined herein, that are associated with or caused by Down's syndrome.

"Rett's syndrome" or cerebroatrophic hyperammonemia is a progressive syndrome characterized by symptoms of autism, dementia, cognitive impairments, ataxia, and/or purposeless hand movements. In preferred embodiments, the invention is directed to methods of treating and preventing cognitive impairments, as defined herein, and/or dementia, as defined herein, that are associated with or caused by Rett's syndrome.

"Progressive supranuclear palsy," also known as Steele-Richardson-Olszewksi syndrome, is a rare brain disorder characterized by problems with control of gait and/or balance. The most obvious sign of the disease is an inability to aim the eyes properly, which occurs because of lesions in the area of the brain that coordinates eye movements. Other symptoms of progressive supranuclear palsy include alterations of mood and behavior (e.g., depression, apathy, cognitive impairments, and/or progressive mild dementia). In preferred embodiments, the invention is directed to methods of treating and preventing cognitive impairments, as defined herein, and/or dementia, as defined herein, that are associated with or caused by progressive supranuclear palsy.

"Frontal lobe syndrome" can arise from a variety of causes, including, for example, stroke, head injury, multi-infarct dementia, tumors affecting the frontal lobe, and/or post-encephalitis syndrome. Symptoms of frontal lobe syndrome include mood lability, decrease or loss of judgment and insight, inappropriate or disinhibited behavior, memory deficit, decrease in attention span, inability to shift set of thinking, difficulties in planning and execution of tasks, and/or motor or sensory deficits specific to other brain areas that may be concomitantly impaired. In preferred embodiments, the invention is directed to methods of treating and preventing cognitive impairments, as defined herein, and/or dementia, as defined herein, that are associated with or caused by frontal lobe syndrome.

"Schizophrenia" is a psychosis characterized by a disorder in the thinking processes, such as delusions and hallucinations, and extensive withdrawal of the patient's interest from other people and the outside world, and the investment of it in his own. Patients diagnosed with schizophrenia often have cognitive impairments and/or dementia caused by the underlying disease process and/or as a side-effect of the treatments with antipsychotic medications. In preferred embodiments, the invention is directed to methods of treating and preventing cognitive impairments, as defined herein, and/or dementia, as defined herein, that are associated with or caused by schizophrenia and related psychiatric/psychological disorders (including, for example, schizoaffective disorders). In alternative embodiments, the invention is directed to methods of treating and preventing cognitive impairments, as defined herein, and/or dementia, as defined herein, that are a side-effect of antipsychotic medications. As used herein, the term "schizophrenia" refers to reactive and process schizophrenias, including, for example, chronic schizophrenia, ambulatory schizophrenia, catatonic schizophrenia, disorganized schizophrenia, latent schizophrenia, paranoid schizophrenia, pseudoneurotic schizophrenia, residual schizophrenia, and simple schizophrenia.

"Cognitive impairments caused by traumatic brain injury" refers to cognitive impairments, as defined herein, that are associated with or caused by traumatic brain injury, including post-head trauma and other traumas to the head, such as, for example, traumas caused by accidents and/or sports injuries. "Cognitive impairments caused by traumatic brain injury" includes dementia pugilistica, which is severe brain damage caused by repeated blows to the head (e.g., from boxing). Dementia pugilistica is a chronic and progressive clinical syndrome characterized by neurological evidence of damage to pyramidal, extrapyramidal, and cerebellar systems with associated psychosis, dementia, personality change and impaired social functioning and/or prominent signs/symptoms of Parkinsonism (e.g., tremors, dysarthria, rigidity, bradykinesia, other extrapyramidal signs).

"Cognitive impairments caused by post coronary artery by-pass graft surgery" refers to cognitive impairments, as defined herein, that are caused by or associated with post coronary artery by-pass graft surgery or ischemic vascular disease.

"Cognitive impairments associated with electroconvulsive shock therapy" refers to cognitive impairments, as defined herein, that are caused by or associated with electroconvulsive shock therapy. In other embodiments, the invention is directed to alleviating (e.g., reducing or eliminating) the cognitive impairments caused by the seizures that follow electroconvulsive shock therapy by administering a therapeutically effective amount of at least one of the cholinesterase inhibitor compounds described herein.

"Cognitive impairments associated with chemotherapy" refers to cognitive impairments, as defined herein, that are caused by or associated with chemotherapy. In other embodiments, the invention is directed to alleviating (e.g., reducing or eliminating) the cognitive impairments that are associated with chemotherapy by administering a therapeutically effective amount of at least one of the cholinesterase inhibitor compounds described herein. In a preferred embodiment, the invention describes novel methods for treating or preventing cognitive impairments in breast cancer patients undergoing chemotherapy by administering a therapeutically effective amount of at least one of the cholinesterase inhibitor compounds described herein.

"Delirium" refers to a clouded state of consciousness and confusion that is marked by difficulty in sustaining attention to stimuli, disordered thinking, defective perceptions, illusions, hallucinations, disordered sleep-wakefulness cycles, and/or motor disturbances. There are various categories of delirium covered by the invention, including, for example, post-operative delirium (where the onset of the delirium is after an operation) anxious delirium (in which the predominating symptom is an incoherent apprehension or anxiety); collapse delirium (caused by extreme physical depression induced by a shock, profuse hemorrhage, exhausting labor, and the like); low delirium (in which there is little excitement, either mental or motor, where ideas are confused and incoherent but follow each other slowly); muttering delirium (common in low fevers in which the patient is unconscious but constantly muttering incoherently); posttraumatic delirium (a posttraumatic neuropsychologic disorder of the brain with disturbed consciousness, agitation, hallucinations, delusions and/or disorientation); toxic delirium (caused by a poison); and tremens delirium (a form of acute organic brain syndrome due to alcoholic withdrawal and marked by sweating, tremor, atonic dyspepsia, restlessness, anxiety, precordial distress, mental confusion, and hallucinations).

"Tourette's syndrome" is characterized by motor incoordination, echolalia (i.e., repetition of what is said by other people) and/or coprolalia (i.e., involuntary utterances of vulgar or obscene words). Tourette's syndrome is a form of tic.

"Myasthenia gravis" refers to any chronic progressive muscular weakness. Myasthenia gravis includes Goldflam or Hoppe-Goldflam disease. Myasthenia gravis is thought to be caused by a defect in myoneural conduction. As used herein, "myasthenia gravis" includes Lambert-Eaton syndrome or carcinomatous myopathy, which is a progressive proximal muscle weakness in patients with carcinoma, generally in the absence of dermatomyositis orpolymyositis. Lambert-Eaton syndrome is thought to be caused by antibodies directed against motor-nerve axon terminals.

"Attention deficit hyperactivity disorder" (ADHD) is a neurological condition where the patient, including adults and children, has a reduced ability to maintain attention without distraction, has a reduced ability to control doing or saying something due to impulsivity, has a lack of appropriate forethought, and/or is restless. In preferred embodiments, the invention is directed to methods of treating and preventing cognitive impairments, as defined herein, that are associated with or caused by attention deficit hyperactivity disorder. In alternative embodiments, the invention is directed to methods of treating the attentional symptoms associated with or caused by attention deficit hyperactivity disorder.

"Autism" is a complex developmental disability that affects the functioning of the brain, and typically appears in a patient by the age of three. Autism impacts the normal development of the brain in the areas of social interaction and communication skills. Patients with autism typically have difficulties in verbal and non-verbal communication, social interactions, and/or leisure or play activities. The disorder makes it hard for them to communicate with others and relate to the outside world. In some cases, aggressive and/or self-injurious behavior may be present. Patients with autism may experience sensitivities in the senses, exhibit repeated body movements (e.g., hand flapping, rocking), have unusual responses to people or attachments to objects and/or resistance to changes in routines.

"Dyslexia" is characterized by one or more of the following: a memory instability for letters, words, or numbers; tendency to skip over or scramble letters, words, and sentences; poor reading ability; poor concentration; distractibility; photophobia; tunnel; vision, delayed visual and phonetic processing; poor handwriting prone to size, spacing, and letter-sequencing errors; memory instability for spelling, grammar, math, names, dates, and lists; speech disorders such as slurring, stuttering, minor articulation errors, poor word recall, and auditory-input and motor-output speech lags; impaired concentration, distractibility, hyperactivity, or overactivity; difficulties with balance and coordination functions; headaches, nausea, dizziness, vomiting, motion sickness, abdominal complaints, excessive sweating, and bed-wetting; and/or poor self-esteem.

"Mania" is an emotional disorder characterized by symptoms of euphoria, increased psychomotor activity, rapid speech, flight of ideas, decreased need for sleep, distractibility, irritability, increased sexual desire, increased energy, grandiosity, and/or poor judgment. "Hypomania" refers to a mild form of mania. Mania and hypomania often occur in bipolar disorder.

"Depression" refers to and includes major depression, dysthymia and bioplar disorder. Major depression is characterized by a persistent sad, anxious and/or empty mood; feelings of hopelessness, pessimism, guilt, worthlessness, and/or helplessness; a loss of interest or pleasure in hobbies and activities, including sex; decreased energy or fatigue; difficulty concentrating, remembering and/or making decisions; insomnia, early-morning awakening or oversleeping; increased or decreased appetite; thoughts of suicide or death;

suicide attempts; restlessness and/or irritability; and/or persistent physical symptoms that do not respond to treatment, such as headaches, digestive disorders and/or chronic pain. Major depression can be characterized by a few or many symptoms which can vary over time. Dysthymia refers to a less severe (sometimes chronic) form of major depression. Bipolar disorder, also called manic-depressive illness, is characterized by cycling mood changes from highs (e.g., mania) to lows (e.g., major depression or dysthymia).

"Apathy" refers to a slowing of cognitive processes and/or a lack of motivation as manifested by one or more of the following: lack of productivity, lack of initiative, lack of perseverance, diminished socialization or recreation, lack of interest in learning new things, lack of interest in new experiences, lack of emotional responsivity to positive or negative events, unchanging or flat affect, and/or absence of excitement or emotional intensity.

"Enhancing cognitive functions" refers to increasing or improving a patient's normal level of cognitive functioning, including, for example, learning and recall of newly learned information. In the methods of enhancing cognitive functions described herein, the patient is administered at least one of the cholinesterase inhibitors described herein for about 1 to about 7 days prior to the time when improved cognitive function is required or desired.

"Sleep apnea" can be characterized by sleep symptoms and daytime symptoms. Sleep symptoms can include, for example, snoring, restless sleep, sleep disruptions, choking, esophageal reflux, nocturia, heavy sweating and the like. Day time symptoms can include, for example, hypersomnolence, morning headaches, mood alterations, sexual dysfunctions, hearing loss, automatic behavior, short term memory loss and hypnogenic hallucinations. "Sleep apnea" includes obstructive sleep apnea syndrome and central sleep apnea, both of which are characterized by repetitive episodes of upper airway obstruction that occur during seep.

"Alleviating tobacco withdrawal syndrome" refers to reducing or eliminating at least one symptom that occurs when a person stops using a product containing nicotine. The symptoms that generally occur in tobacco withdrawal syndrome include one or more of cravings for tobacco or nicotine, irritability, insomnia, impatience, restlessness, difficulty concentrating, increased appetite (which can include weight gain), and/or decreased heart rate. The phrase "stops using a product containing nicotine" refers to a patient who ceases or attempts to cease, either permanently or temporarily, from smoking cigarettes, cigars, pipes, other forms of tobacco, and/or other nicotine-containing products, and/or using chewing tobacco, or other nicotine-containing products.

Huntington's disease is a genetic degenerative brain disorder. The "behavioral dysfunctions in Huntington's disease" includes one or more symptoms of aggressive outbursts, impulsiveness, mood swings and/or social withdrawal. The "cognitive dysfunctions in Huntington's disease" includes one or more symptoms of the "cognitive impairments" defined herein. The cholinesterase inhibitors of the invention can also be used to treat the motor dysfunctions in Huntington's disease, including, for example, nervous activity, fidgeting, twitching, excessive restlessness, reduced coordination and the like. The cholinesterase inhibitors of the invention can also be used to treat the emotional dysfunctions in Huntington's disease including, for example, depression, irritability, anxiety, apathy and the like.

In another embodiment, the cholinesterase inhibitors of the invention are used to treat the dysfunctions caused by Juvenile Huntington's Disease, also known as the Westphal variant, that affects children. Symptoms of Juvenile Huntington's Disease include slow, stiff and awkward walking and talking, choking, clumsiness and falling, and also include the "cognitive impairments" defined herein.

In each of the methods described herein, the cholinesterase inhibitors of the invention alleviate (e.g., reduce or eliminate) at least one (preferably two, three, or all) symptom of the disease, disorder or syndrome being treated. Preferably, the cholinesterase inhibitors are alleviating the symptoms of cognitive impairments and/or dementia.

As described and defined herein, the invention is directed to novel methods for treating and preventing dementia caused by vascular diseases; dementia associated with Parkinson's disease; Lewy Body dementia; AIDS dementia; mild cognitive impairments; age-associated memory impairments; cognitive impairments and/or dementia associated with neurologic and/or psychiatric conditions, including epilepsy, brain tumors, brain lesions, multiple sclerosis, Down's syndrome, Rett's syndrome, progressive supranuclear palsy, frontal lobe syndrome, and schizophrenia and related psychiatric disorders; cognitive impairments caused by traumatic brain injury, post coronary artery by-pass graft surgery, electroconvulsive shock therapy, and chemotherapy; and to novel methods for treating and preventing delirium, Tourette's syndrome, myasthenia gravis, attention deficit hyperactivity disorder, autism, dyslexia, mania, depression, apathy, and myopathy associated with diabetes; and to novel methods for delaying the onset of Alzheimer's disease; for enhancing cognitive functions; for treating and preventing sleep apnea, and for alleviating tobacco withdrawal syndrome, and for treating the dysfunctions of Huntington's disease by administering to a patient in need thereof a therapeutically effective amount of at least one cholinesterase inhibitor of formula I or a pharmaceutically acceptable salt thereof:

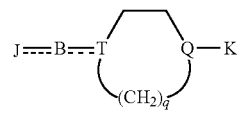

I wherein J is
(a) a substituted or unsubstituted group selected from the group consisting of (1) phenyl, (2) pyridyl, (3) pyrazyl, (4) quinolyl, (5) cyclohexyl, (6) quinoxalyl, and (7) furyl;
(b) a monovalent or divalent group, in which the phenyl may have one or more substituents selected from (1) indanyl, (2) indanonyl, (3) indenyl, (4) indenonyl, (5) indanedionyl, (6) tetralonyl, (7) benzosuberonyl, (8) indanolyl, and (9) $C_6H_5$—CO—CH(CH$_3$)—;
(c) a monovalent group derived from a cyclic amide compound;
(d) a lower alkyl group; or
(e) a group of $R^{21}$—CH=CH—, in which $R^{21}$ is hydrogen or a lower alkoxycarbonyl group;

B is —(CHR$^{22}$)$_r$—, —CO—(CHR$^{22}$), —NR$^4$—(CHR$^{22}$)$_r$—, —CO—NR$^5$—(CHR$^{22}$)$_r$—, —CH=CH—(CHR$^{22}$)$_r$—, —OCOO—(CHR$^{22}$)$_r$—, —OOC—NH—(CHR$^{22}$)$_r$—, NH—CO—(CHR$^{22}$)$_r$—, —CH$_2$—CO—NH—(CHR$^{22}$)$_r$, —(CH$_2$)$_2$—NH—(CHR$^{22}$)$_r$—, —CH(OH)—(CHR$^{22}$)$_r$—, =(CH—CH=CH)$_b$—, =CH—(CH$_2$)$_c$—, =(CH—CH)$_d$=, —CO—CH=CH—CH$_2$—, —CO—CH$_2$—CH(OH)—CH$_2$—, —CH(CH$_3$)—CO—NH—

CH$_2$—, —CH=CH=CO—NH—(CH$_2$)$_2$—, —NH—, —O—, —S—, a dialkylaminoalkyl-carbonyl or a lower alkoxycarbony;

wherein R$^4$ is hydrogen, lower alkyl, acyl, lower alkylsulfonyl, phenyl, substituted phenyl, benzyl, or substituted benzyl; R$^5$ is hydrogen, lower alkyl or phenyl; r is zero or an integer of about 1 to about 10; R$^{22}$ is hydrogen or methyl so that one alkylene group may have no methyl branch or one or more methyl branches; b is an integer of about 1 to about 3; c is zero or an integer of about 1 to about 9; d is zero or an integer of about 1 to about 5;

T is nitrogen or carbon;

Q is nitrogen, carbon or

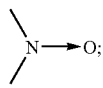

q is an integer of about 1 to about 3;

K is hydrogen, phenyl, substituted phenyl, arylalkyl in which the phenyl may have a substituent, cinnamyl, a lower alkyl, pyridylmethyl, cycloalkylalkyl, adamantanemethyl, furylmenthyl, cycloalkyl, lower alkoxycarbonyl or an acyl; and ---- is a single bond or a double bond.

In the compound of formula I, J is preferably (a) or (b), more preferably (b). In the definition of (b), a monovalent group (2), (3) and (5) and a divalent group (2) are preferred. The group (b) preferably includes, for example, the groups having the formulae shown below:

indanyl
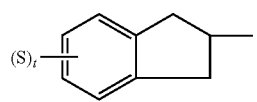

tetralonyl
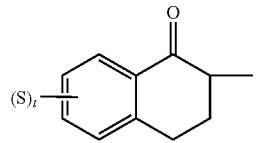

indanonyl
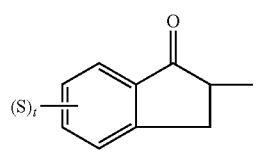

benzosuberonyl
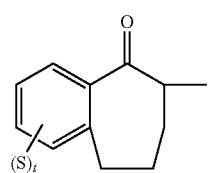

indanonylidenyl
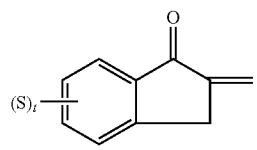

-continued indanolyl
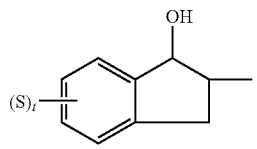

indenyl
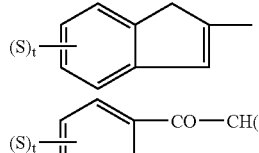

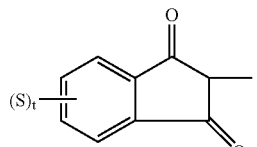

indanedionyl
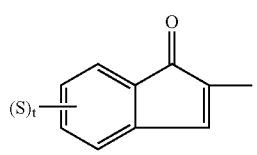

indenonyl wherein t is an integer of about 1 to about 4; and each S is independently hydrogen or a substituent, such as a lower alkyl having 1 to 6 carbon atoms or a lower alkoxy having 1 to 6 carbon atoms. Among the substituents, methoxy is most preferred. The phenyl is most preferred to have 1 to 3 methoxy groups thereon. (S)$_t$ may form methylene dioxy groups or ethylene dioxy groups on two adjacent carbon atoms of the phenyl group. Of the above groups, indanonyl, indanedionyl and indenyl, optionally having substituents on the phenyl, are the most preferred.

In the definition of B, —(CHR$^{22}$)$_r$—, —CO—(CHR$^{22}$)$_r$—, =(CH—CH=CH)$_b$—, =CH—(CH$_2$)$_c$— and =(CH—CH)$_d$= are preferable. The group of —(CHR$^{22}$)$_n$— in which R$^{22}$ is hydrogen and r is an integer of 1 to 3, and the group of =CH—(CH$_2$)$_n$— are most preferable. The preferable groups of B can be connected with (b) of J, in particular (b)(2).

The ring containing T and Q in formula I can be 5-, 6- or 7-membered. It is preferred that Q is nitrogen, T is carbon or nitrogen, and q is 2; or that Q is nitrogen, T is carbon, and q is 1 or 3; or that Q is carbon, T is nitrogen and q is 2.

It is preferable that K is a phenyl, arylalkyl, cinnamyl, phenylalkyl or a phenylalkyl having a substituent(s) on the phenyl.

In preferred embodiments, the cyclic amine compounds of formula I are the piperidine compounds of formula II or a pharmaceutically acceptable salt thereof:

II
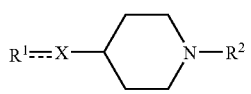

wherein R$^1$ is a (1) substituted or unsubstituted phenyl group; (2) a substituted or unsubstituted pyridyl group; (3) a substituted or unsubstituted pyrazyl group; (4) a substituted or unsubstituted quinolyl group; (5) a substituted or unsubstituted indanyl group; (6) a substituted or unsubstituted cyclohexyl group; (7) a substituted or unsubstituted quinoxalyl group; (8) a substituted or unsubstituted furyl group; (9) a monovalent or divalent group derived from an indanone having a substituted or unsubstituted phenyl ring; (10) a monovalent group derived from a cyclic amide compound; (11) a lower alkyl group; or (12) a group of the formula $R^3$—CH=C—, where $R^3$ is a hydrogen atom or a lower alkoxycarbonyl group;

X is —$(CH_2)_n$—, —C(O)—$(CH_2)_n$—, —$N(R^4)$—$(CH_2)_n$—, —C(O)—$N(R^5)$—$(CH_2)_n$—, —CH=CH—$(CH_2)_n$—, —O—C(O)—O—$(CH_2)_n$—, —O—C(O)—NH—$(CH_2)_n$—, —CH=CH—CH=CO—, —NH—C(O)—$(CH_2)_n$—, —$CH_2$—C(O)—NH—$(CH_2)_n$—, —$(CH_2)_2$—C(O)—NH—$(CH_2)_n$—, —CH(OH)—$(CH_2)_n$—, —C(O)—CH=CH—$CH_2$—, —C(O)—$CH_2$—CH(OH)—$CH_2$—, —$CH(CH_3)$—C(O)—NH—$CH_2$—, —CH=CH—C(O)—NH—$(CH_2)_2$—, a dialkylaminoalkylcarbonyl group, a lower alkoxycarbonyl group;

where n is an integer of 0 to 6; $R^4$ is a hydrogen atom, a lower alkyl group, an acyl group, a lower alkylsulfonyl group, a substituted or unsubstituted phenyl group, or a substituted or unsubstituted benzyl group; and $R^5$ is a hydrogen atom a lower alkyl group or a phenyl group;

$R^2$ is a substituted or unsubstituted phenyl group; a substituted or unsubstituted arylalkyl group; a cinnamyl group; a lower alkyl group; a pyridylmethyl group; a cycloalkylalkyl group; an adamantanemethyl group; or a furoylmethyl group; and ----- is a single bond or a double bond.

The term "lower alkyl group" as used herein means a straight or branched alkyl group having 1 to 6 carbon atoms. Exemplary "lower alkyl groups" include methyl, ethyl, propyl, isopropyl, butyl, isobutyl, sec-butyl, tert-butyl, pentyl (amyl), isopentyl, neopentyl, tert-pentyl, 1-methylbutyl, 2-methylbutyl, 1,2-dimethylpropyl, hexyl, isohexyl, 1-methylpentyl, 2-methyl-pentyl, 3-methylpentyl, 1,1-dimethylbutyl, 1,2-dimethylbutyl, 2,2-dimethylbutyl, 1,3-dimthylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, and the like. The lower alkyl group is preferably methyl, ethyl, propyl or isopropyl; more preferably methyl.

Specific examples of the substituents for the substituted or unsubstituted phenyl, pyridyl, pyrazyl, quinolyl, indanyl, cyclohexyl, quinoxalyl and furyl groups in the definition of $R^1$ include lower alkyl groups having 1 to 6 carbon atoms, such as methyl, ethyl, n-propyl, isopropyl, n-butyl, isobutyl, and tert-butyl groups; lower alkoxy groups corresponding to the above-described lower alkyl groups, such as methoxy and ethoxy groups; a nitro group; halogen atoms, such as chlorine, fluorine and bromine; a carboxyl group; lower alkoxycarbonyl groups corresponding to the above-described lower alkoxy groups, such as methoxycarbonyl, ethoxycarbonyl, isopropoxycarbonyl, n-propoxycarbonyl, and n-butyloxycarbonyl groups; an amino group; a lower monoalkylamino group; a lower dialkylamino group; a carbamoyl group; acylamino groups derived from aliphatic saturated monocarboxylic acids having 1 to 6 carbon atoms, such as acetylamino, propionylamino, butyrylamino, isobutyrylamino, valerylamino, and pivaloylamino groups; cycloalkyloxycarbonyl groups, such as a cyclohexyloxycarbonyl group; lower alkylaminocarbonyl groups, such as methylaminocarbonyl and ethylaminocarbonyl groups; lower alkylcarbonyloxy groups corresponding to the above-defined lower alkyl groups, such as methylcarbonyloxy, ethylcarbonyloxy, and n-propylcarbonyloxy groups; halogenated lower alkyl groups, such as a trifluoromethyl group; a hydroxyl group; a formyl group; and lower alkoxy lower alkyl groups, such as ethoxymethyl, methoxymethyl and methoxyethyl groups. The "lower alkyl groups" and "lower alkoxyl groups" in the above description of the substituent include all the groups derived from the above-mentioned groups. The substituent may be one to three of them, which may be the same or different.

When the substituent is a phenyl group, the following group is within the scope of the substituted phenyl group:

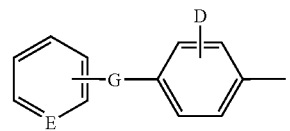

wherein G is —C(O)—, —O—C(O)—, —O—, —$CH_2$—NH—C(O)—, —$CH_2$—O—, —$CH_2$—$SO_2$—, —CH(OH)—, or —$CH_2$—S(→O)—; E is a carbon or nitrogen atom; and D is a substituent.

Preferred examples of the substituents (i.e., "D") for the phenyl group include lower alkyl, lower alkoxy, nitro, halogenated lower alkyl, lower alkoxycarbonyl, formyl, hydroxyl, and lower alkoxy lower alkyl groups, halogen atoms, and benzyol and benzylsulfonyl groups. The substituent may be two or more of them, which may be the same or different.

Preferred examples of the substituent for the pyridyl group include lower alkyl and amino groups and halogen atoms.

Preferred examples of the substituent for the pyrazyl group include lower alkoxycarbonyl, carboxyl, acylamino, carbamoyl, and cycloalkyloxycarbonyl groups.

With respect to $R^1$, the pyridyl group is preferably a 2-pyridyl, 3-pyridyl, or 4-pyridyl group; the pyrazyl group is preferably a 2-pyrazinyl group; the quinolyl group is preferably a 2-quinolyl or 3-quinolyl group; the quinoxalinyl group is preferably a 2-quinoxalinyl or 3-quinoxalinyl group; and the furyl group is preferably a 2-furyl group.

Specific examples of preferred monovalent or divalent groups derived from an indanone having an unsubstituted or substituted phenyl ring include those represented by formulas (A) and (B):

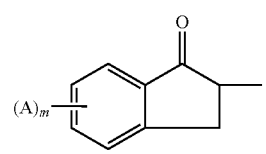

(A)

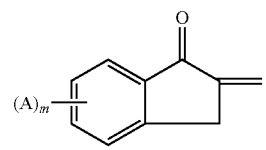

(B)

where m is an integer of from 1 to 4, and each A is independently a hydrogen atom, a lower alkyl group, a lower alkoxy group, a nitro group, a halogen atom, a carboxyl group, a lower alkoxycarbonyl group, an amino group, a lower monoalkylamino group, a lower dialkylamino group, a carbamoyl group, an acylamino group derived from aliphatic saturated monocarboxylic acids having 1 to 6 carbon atoms, a cycloalkyloxycarbonyl group, a lower alkylaminocarbonyl group, a lower alkylcarbonyloxy group, a halogenated lower alkyl group, a hydroxyl group, a formyl group, or a lower alkoxy lower alkyl group; preferably a hydrogen atom, a lower alkyl group or a lower alkoxy group; most preferably the indanone group is unsubstituted or substituted with 1 to 3 methoxy groups.

Examples of the monovalent group derived from a cyclic amide compound include quinazolone, tetrahydroisoquinolinone, tetrahydrobenzodiazepinone, and hexahydrobenzazocinone. However, the monovalent group may be any one having a cyclic amide group in the structural formula thereof, and is not limited to the above-described specific examples. The cyclic amide group may be one derived from a monocyclic or condensed heterocyclic ring. The condensed heterocyclic ring is preferably one formed by condensation with a phenyl ring. In this case, the phenyl ring may be substituted with a lower alkyl group having 1 to 6 carbon atoms, preferably a methyl group, or a lower alkoxy group having 1 to 6 carbon atoms, preferably a methoxy group.

Preferred examples of the monovalent group include the following:

(a)
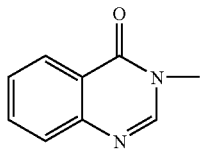

(b)
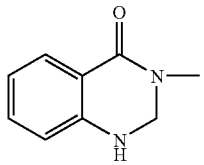

(c)
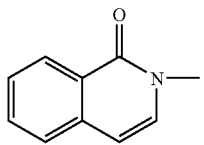

(d)
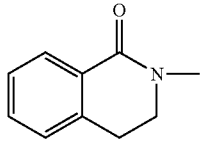

(e)
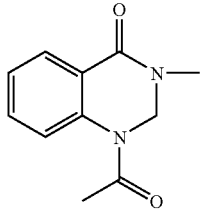

(f)
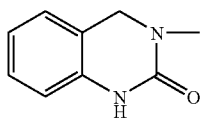

-continued (g)
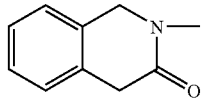

(h)
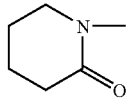

(i)
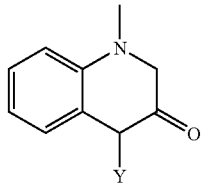

(j)
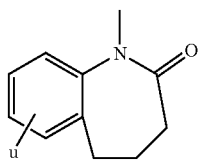

(k)
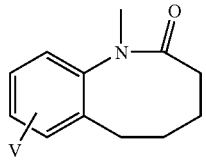

(l)
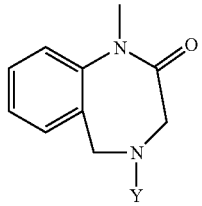

(m)
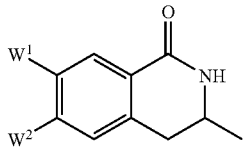

(n)
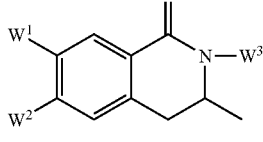

In the above formulae, Y is a hydrogen atom or a lower alkyl group; V and U are each a hydrogen atom or a lower alkoxy group (preferably dimethoxy); $W^1$ and $W^2$ are each a hydrogen atom, a lower alkyl group, or a lower alkoxy group; and $W^3$ is a hydrogen atom or a lower alkyl group. The right hand ring in formulae (j) and (l) is a 7-membered ring, while the right hand ring in formula (k) is an 8-membered ring.

The most preferred examples of the above-defined $R^1$ include a monovalent group derived from an indanone having an unsubstituted or substituted phenyl group and a monovalent group derived from a cyclic amide compound.

The most preferred examples of the above-defined X include —(CH$_2$)$_n$—, an amide group, or groups represented by the above formulae where n is 2. Thus, it is most preferred that any portion of a group represented by the formula R$^1$----X— have a carbonyl or amide group.

The substituents involved in the expressions "a substituted or unsubstituted phenyl group" and "a substituted or unsubstituted arylalkyl group" in the above definition of R$^2$ are the same substituents as those described for the above definitions of a phenyl group, a pyridyl group, a pyrazyl group, a quinolyl group, an indanyl group, a cyclohexyl group, a quinoxalyl group or a furyl group in the definition of R$^1$.

The term "arylalkyl group" is intended to mean an unsubstituted benzyl or phenethyl group or the like.

Specific examples of the pyridylmethyl group include 2-pyridylmethyl, 3-pyridylmethyl, and 4-pyridylmethyl groups.

Preferred examples of R$^2$ include benzyl and phenethyl groups. The symbol ----means a double or single bond. The bond is a double bond only when R$^1$ is the divalent group (B) derived from an indanone having an unsubstituted or substituted phenyl ring, while it is a single bond in other cases.

In preferred embodiments, the compound of formula II is a compound of formula III or a pharmaceutically acceptable salt thereof:

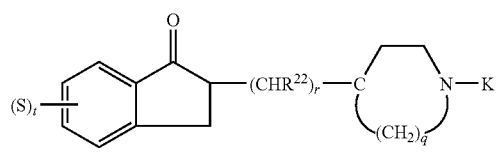

III wherein r is an integer of about 1 to about 10; each R$^{22}$ is independently hydrogen or methyl; K is a phenalkyl or a phenalkyl having a substituent on the phenyl ring; each S is independently a hydrogen, a lower alkyl group having 1 to 6 carbon atoms or a lower alkoxy group having 1 to 6 carbon atoms; t is an integer of 1 to 4; q is an integer of about 1 to about 3; with the proviso that (S)$_t$ can be a methylenedioxy group or an ethylenedioxy group joined to two adjacent carbon atoms of the phenyl ring.

In preferred embodiments, the compound of formula III is:
1-benzyl-4-((5,6-dimethoxy-1-indanon)-2-yl)methylpiperidine,
1-benzyl-4-((5,6-dimethoxy-1-indanon)-2-ylidenyl)methylpiperidine,
1-benzyl-4-((5-methoxy-1-indanon)-2-yl)methylpiperidine,
1-benzyl-4-((5,6-diethoxy-1-indanon)-2-yl)methylpiperidine,
1-benzyl-4-((5,6-methnylenedioxy-1-indanon)-2-yl)methylpiperidine,
1-(m-nitrobenzyl)-4-((5,6-dimethoxy-1-indanon)-2-yl)methylpiperidine,
1-cyclohexylmethyl-4-((5,6-dimethoxy-1-indanon)-2-yl)methylpiperidine,
1-(m-fluorobenzyl)-4-((5,6-dimethoxy-1-indanon)-2-yl)methylpiperidine,
1-benzyl-4-((5,6-dimethoxy-1-indanon)-2-yl)propylpiperidine,
1-benzyl-4-((5-isopropoxy-6-methoxy-1-indanon)-2-yl)methylpiperidine,
1-benzyl-4-((5,6-dimethoxy-1-oxoindanon)-2-yl)propenylpiperidine; or
pharmaceutically acceptable salts thereof.

In more preferred embodiments, the compound of formula III is 1-benzyl-4-((5,6-dimethoxy-1-indanon)-2-yl)methylpiperidine or a pharmaceutically acceptable salt thereof. In the most preferred embodiment, the compound of formula III is 1-benzyl-4-((5,6-dimethoxy-1-indanon)-2-yl)methylpiperidine hydrochloride, which is also known as donepezil hydrochloride or ARICEPT® (Eisai Inc., Teaneck, N.J.), and which has formula IV:

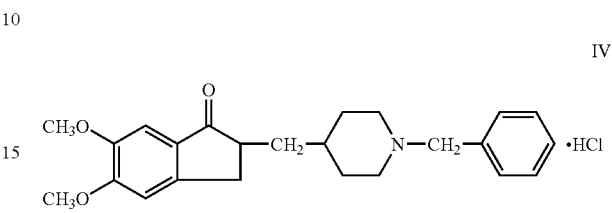

IV

The compounds of the invention may have an asymmetric carbon atom(s), depending upon the substituents, and can have stereoisomers, which are within the scope of the invention. For example, donepezil hydrochloride can be in the forms described in Japanese Patent Application Nos. 4-187674 and 4-21670, the disclosures of which are incorporated by reference herein in their entirety. Japanese Patent Application No. 4-187674 describes a compound having formula V:

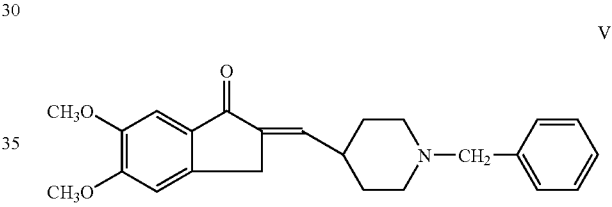

V which can be in the form of a pharmaceutically acceptable salt, such as a hydrochloride salt. Japanese Patent Application No. 4-21670 describes compounds having formula VI:

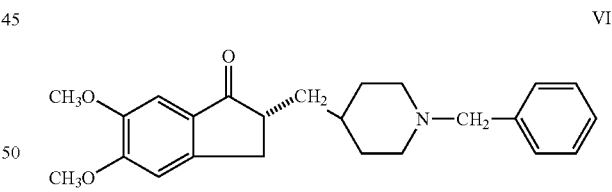

VI which can be in the form of a pharmaceutically acceptable salt, such as a hydrochloride salt; and compounds of formula VII:

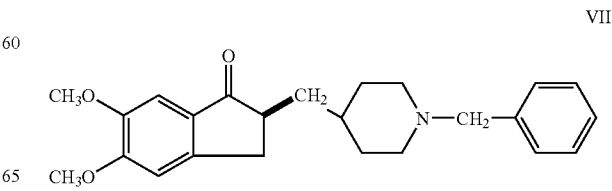

VII which can be in the form of a pharmaceutically acceptable salt, such as a hydrochloride salt; and compounds of formula VIII:

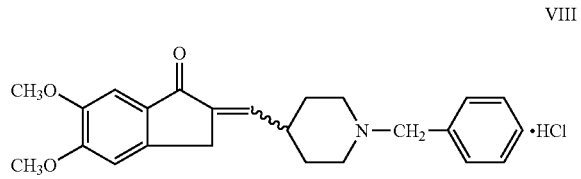

VIII

As described above, the compounds of the invention can be administered in the form of a pharmaceutically acceptable salt. Pharmaceutically acceptable salts are known in the art and include those of inorganic acids, such as hydrochloride, sulfate, hydrobromide and phosphate; and those of organic acids, such as formate, acetate, trifluoroacetate, methanesulfonate, benzenesulfonate and toluenesulfonate. When certain substituents are selected, the compounds of the invention may form, for example, alkali metal salts, such as sodium or potassium salts; alkaline earth metal salts, such as calcium or magnesium salts; organic amine salts, such as a salt with trimethylamine, triethylamine, pyridine, picoline, dicyclohexylamine or N,N'-dibenzylethylenediamine. One skilled in the art will recognize that the compounds of the invention can be made in the form of any other pharmaceutically acceptable salt.

The compounds of the invention can be prepared by processes that are known in the art and described, for example, in U.S. Pat. No. 4,895,841, WO 98/39000, and Japanese Patent Application Nos. 4-187674 and 4-21670, the disclosures of each of which are incorporated by reference herein in their entirety. Donepezil hydrochloride, a preferred cholinesterase inhibitor for use in the methods described herein, is commercially available as ARICEPT® from Eisai Inc., Teaneck, N.J.

The dosage regimen for treating the diseases described herein with the cholinesterase inhibitors described herein is selected in accordance with a variety of factors, including the age, weight, sex, and medical condition of the patient, the severity of the disease, the route of administration, pharmacological considerations such as the activity, efficacy, pharmacokinetic and toxicology profiles of the particular cholinesterase inhibitor used, whether a drug delivery system is used and whether the cholinesterase inhibitor is administered as part of a drug combination. Thus, the dosage regimen actually used may vary widely and may deviate from the preferred dosage regimen described herein.

In preferred embodiments, the cholinesterase inhibitors of the invention are administered to treat the diseases described herein in doses of about 0.1 milligram to about 300 milligrams per day, preferably about 1 milligram to about 100 milligrams per day, more preferably about 5 milligrams to about 10 milligrams per day. The doses can be administered in one to four portions over the course of a day, preferably once a day. One skilled in the art will recognize that when the cholinesterase inhibitors of the invention are administered to children, the dose may be smaller than the dose administered to adults, and that the dose can be dependent upon the size and weight of the patient. In preferred embodiments, a child can be administered the cholinesterase inhibitors of the invention in doses of about 0.5 milligrams to about 10 milligrams per day, preferably about 1 milligram to about 3 milligrams per day.

In preferred embodiments of the methods described herein, a physician can administer patients donepezil hydrochloride, which is commercially available as ARICEPT® (Eisai Inc., Teaneck, N.J.), as film-coated tablets containing 5 milligrams donepezil hydrochloride or 10 milligrams donepezil hydrochloride. The tablets can be administered one to about four times a day. In preferred embodiments, one 5 milligram or one 10 milligram ARICEPT® tablet is administered once a day for the methods described herein. One skilled in the art will appreciate that when donepezil hydrochloride is administered to children, the dose may be smaller than the dose that is administered to adults. In preferred embodiments, a child can be administered donepezil hydrochloride in doses of about 0.5 milligrams to about 10 milligrams per day, preferably about 1 milligram to about 3 milligrams per day.

The cholinesterase inhibitors of the invention can be administered orally, topically, parenterally, by inhalation (nasal or oral), or rectally in dosage unit formulations containing conventional nontoxic pharmaceutically acceptable carriers, adjuvants, and vehicles as desired. The term parenteral as used herein includes subcutaneous, intravenous, intramuscular, intrasternal injection, or infusion techniques. Preferably, the cholinesterase inhibitors of the invention are orally administered as tablets. When administered to children, the cholinesterase inhibitors of the invention are preferably orally administered in a liquid dosage form. It will also be preferable to orally administer the cholinesterase inhibitors in a liquid dosage form to patients, such as those being treated for schizophrenia or related psychiatric disorders, who are unable to take a solid dosage form. In the methods of alleviating tobacco withdrawal syndrome described herein, the cholinesterase inhibitors can preferably be administered topically, most preferably in the form of a transdermal patch.

Injectable preparations, for example, sterile injectable aqueous or oleaginous suspensions may be formulated according to the known art using suitable dispersing or wetting agents, suspending agents (e.g., methylcellulose, Polysorbate 80, hydroxyethylcellulose, acacia, powdered tragacanth, sodium carboxymethylcellulose, polyoxytehylene sorbitan monolaurate and the like), pH modifiers, buffers, solubilizing agents (e.g., polyoxyethylene hydrogenated castor oil, Polysorbate 80, nicotinamide, polyoxyethylene sorbitan monolaurate, Macrogol, an ethyl ester of castor oil fatty acid, and the like) and preservatives. The sterile injectable preparation may also be a sterile injectable solution or suspension in a nontoxic parenterally acceptable diluent or solvent, for example, as a solution in 1,3-butanediol. Among the acceptable vehicles and solvents that may be used are water, Ringer's solution, and isotonic sodium chloride solution. In addition, sterile, fixed oils are conventionally used as a solvent or suspending medium. For this purpose any bland fixed oil may be used including synthetic mono- or diglycerides, in addition, fatty acids such as oleic acid find use in the preparation of injectables. The preparations can be lyophilized by methods known in the art.

Solid dosage forms for oral administration may include chewing gum, capsules, tablets, sublingual tablets, powders, granules and gels; most preferably tablets. In such solid dosage forms, the active compound may be admixed with one or more inert diluents such as lactose or starch. As is normal practice, such dosage forms may also comprise other substances including lubricating agents such as magnesium stearate. In the case of capsules, tablets, and pills, the dosage forms may also comprise buffering agents. The tablets can be prepared with enteric or film coatings, preferably film coatings.

In addition to the active ingredient, the tablets preferably comprise lactose monohydrate, corn starch, microcrystalline cellulose, hydroxypropyl cellulose, and magnesium stearate;

while the film-coating on the tablet preferably comprises talc, polyethylene glycol, hydroxpropyl methylcellulose, titanium dioxide, and, optionally, other coloring agents, such as yellow iron oxide.

Liquid dosage forms for oral administration can include pharmaceutically acceptable emulsions, solutions, suspensions, and syrups containing inert diluents commonly used in the art, such as water. Such compositions can also comprise adjuvants, such as wetting agents, emulsifying and suspending agents, and sweetening, flavoring, and perfuming agents.

For administration by inhalation, the compositions of the invention can be delivered from an insufflator, a nebulizer or a pressured pack or other convenient mode of delivering an aerosol spray. Pressurized packs can include a suitable propellant. Alternatively, for administration by inhalation, the compositions can be administered in the form of a dry powder composition or in the form of a liquid spray.

Suppositories for rectal administration can be prepared by mixing the active compounds with suitable nonirritating excipients such as cocoa butter and polyethylene glycols that are solid at room temperature and liquid at body temperature.

For topical administration to the epidermis, the cholinesterase inhibitors of the invention can be formulated as ointments, creams or lotions, or as the active ingredient of a transdermal patch. Ointments and creams may, for example, be formulated with an aqueous or oily base with the addition of suitable thickening and/or gelling agents. Lotions may be formulated with an aqueous or oily base and can also generally contain one or more emulsifying agents, stabilizing agents, dispersing agents, suspending agents, thickening agents, and/or coloring agents. The cholinesterase inhibitors can also be administered via iontophoresis.

While the cholinesterase inhibitors of the invention can be administered as the sole active pharmaceutical agent in the methods described herein, they can also be used in combination with one or more compounds which are known to be therapeutically effective against the specific disease that one is targeting for treatment.

Each of the patents and publications cited herein are incorporated by reference herein in their entirety.

It will be apparent to one skilled in the art that various modifications can be made to the invention without departing from the spirit or scope of the appended claims.

What is claimed is:

1. A method for treating dementia or one or more cognitive impairments caused by a brain tumor or chemotherapy, in a patient in need thereof comprising administering to the patient a therapeutically effective amount of a dopepezil or a pharmaceutically acceptable salt thereof, for a time sufficient to alleviate the impairment or the dementia, wherein the therapeutically effective amount is 1 mg to 100 mg.

2. The method of claim 1, wherein donepezil or the pharmaceutically acceptable salt thereof is:

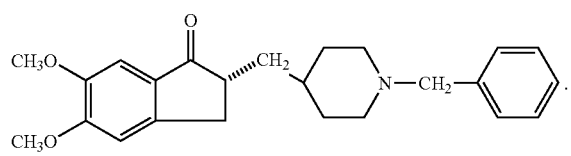

(VI)

3. The method of claim 1, wherein donepezil or the pharmaceutically acceptable salt thereof is:

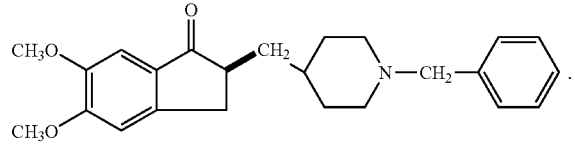

(VII)

4. The method of claim 1, wherein the donepezil or the pharmaceutically acceptable salt thereof, is administered in an amount of 5 mg to 10 mg.

5. The method of claim 1, wherein the donepezil the pharmaceutically acceptable salt thereof is administered in an amount of 5 milligrams.

6. The method of claim 1, wherein the donepezil or the pharmaceutically acceptable salt thereof is administered in an amount of 10 milligrams.

7. The method of claim 1, wherein the donepezil or the pharmaceutically acceptable salt thereof is orally administered.

8. The method of claim 7, wherein donepezil or the pharmaceutically acceptable salt thereof is orally administered in the form of a tablet.

9. The method of claim 1, wherein donepezil or the pharmaceutically acceptable salt thereof is topically administered to the epidermis.

10. The method of claim 1, wherein donepezil or the pharmaceutically acceptable salt thereof is administered by nasal inhalation.

11. The method of claim 1, wherein the method comprises treating dementia or one or more cognitive impairments caused by a brain tumor.

12. The method of claim 1, wherein the method comprises treating one or more cognitive impairments caused by chemotherapy.

13. A method for treating a secondary dementia or one or more cognitive impairments caused by a brain tumor in a patient in need thereof comprising administering to the patient a therapeutically effective amount of donepezil or a pharmaceutically acceptable salt of donepezil for a time sufficient to alleviate the impairment or the dementia, and wherein the therapeutically effective amount is 1 mg to 100 m.

14. A method for treating one or more cognitive impairments caused by chemotherapy in a patient in need thereof comprising administering to the patient a therapeutically effective amount of donepezil or a pharmaceutically acceptable salt of donepezil for a time sufficient to alleviate the impairment, and wherein the therapeutically effective amount is 1 mg to 100 mg.

* * * * *